US00PP16739P3

(12) United States Plant Patent
Meilland

(10) Patent No.: US PP16,739 P3
(45) Date of Patent: Jun. 27, 2006

(54) CLIMBING SHRUB ROSE PLANT NAMED 'MEIVIOWIT'

(50) Latin Name: *Rosa hybrida*
Varietal Denomination: Meiviowit

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 63 days.

(21) Appl. No.: 10/998,820

(22) Filed: Nov. 30, 2004

(65) Prior Publication Data

US 2006/0117422 P1 Jun. 1, 2006

(51) Int. Cl.
*A01H 5/00* (2006.01)

(52) U.S. Cl. ..... Plt./110

(58) Field of Classification Search ..... Plt./110, Plt./103, 114
See application file for complete search history.

*Primary Examiner*—Kent Bell
*Assistant Examiner*—June Hwu
(74) *Attorney, Agent, or Firm*—Buchanan Ingersoll PC

(57) ABSTRACT

A new and distinct variety of climbing shrub rose plant is provided. The new plant is a spontaneous mutation of unknown causation of the 'Meiviolin' variety (U.S. Plant Pat. No. 6,892). Attractive near white long-lasting very double blossoms having an ancient rose configuration are formed on a substantially continuous basis. Vigorous medium green semi-glossy foliage is formed that contrasts well with the near white blossom coloration. Good resistance to Black Spot and good tolerance to frost are displayed. The new variety is particularly well suited for providing attractive ornamentation in the landscape. It can be grown to advantage on a trellis, lamppost or gazebo.

1 Drawing Sheet

Figures 1, 2, 3, 4, 5, 6, 7, 8, 9, 10, 11, 12, 13, 14, 15, 16:
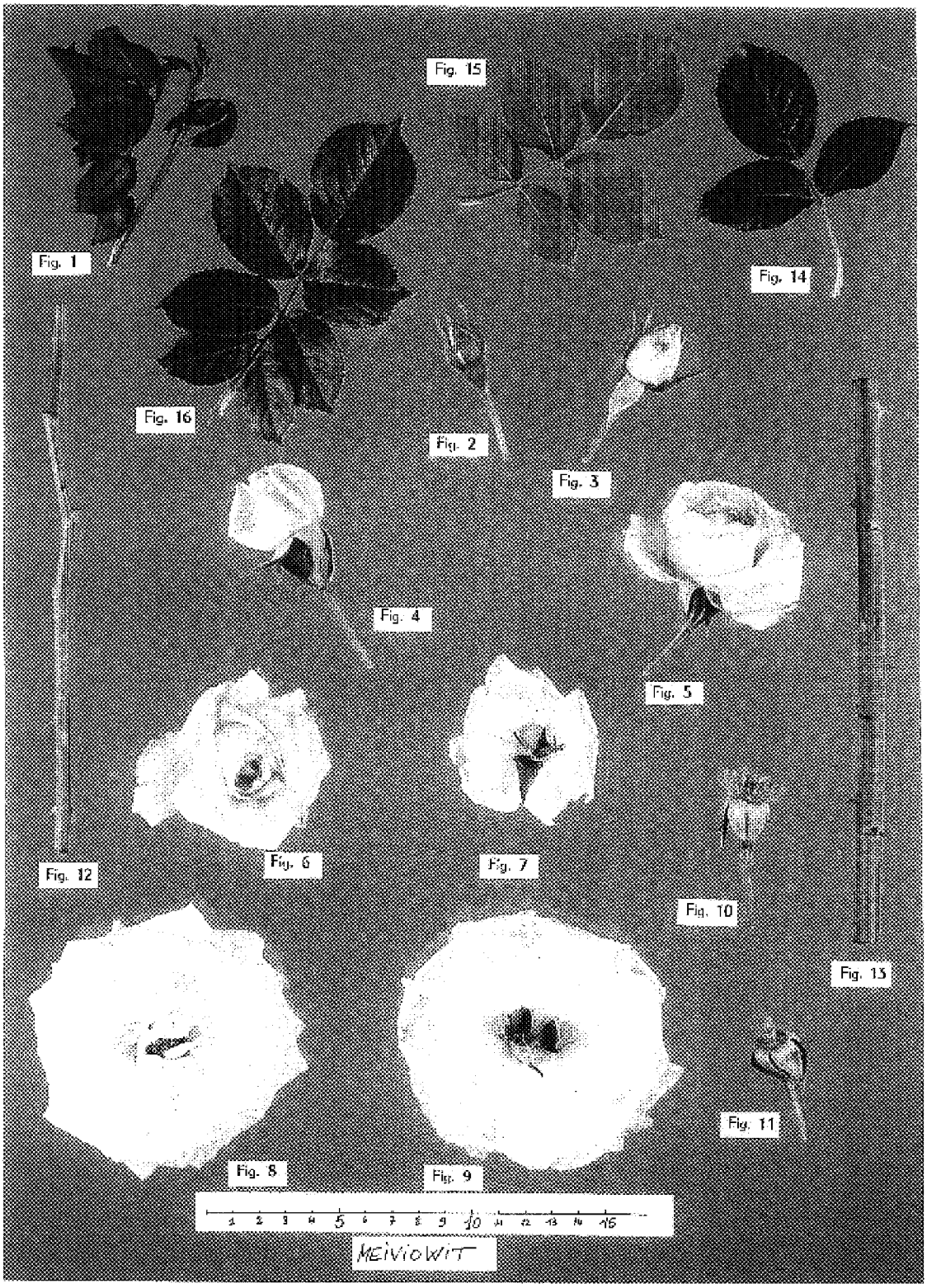

Botanical/commercial classification: *Rosa hybrida*/ Climbing Shrub Rose Plant.
Varietal denomination: cv. Meiviowit.

SUMMARY OF THE INVENTION

The new variety of shrub rose plant was discovered at Le Cannet des Maures, Var, France during July, 1999 while growing in a nursery setting among plants of the 'Meiviolin' variety (U.S. Plant Pat. No. 6,892). This new plant is believed to be a whole plant mutation of unknown causation. Had I not discovered and preserved this new plant it would have been lost to mankind.

It was found that the new rose plant of the present invention displays the following combination of characteristics:

(a) exhibits a climbing shrub growth habit, (b) abundantly forms on a substantially continuous basis attractive near white long-lasting very double blossoms having an ancient rose configuration, (c) forms vigorous medium green semi-glossy foliage that contrasts well with the near white blossom coloration, (d) displays good tolerance to frost, and (e) is well suited for providing attractive ornamentation in the landscape.

The new variety well meets the needs of the horticultural industry and can be grown to advantage in parks and gardens where attractive ornamentation is desired. It is particularly well suited for growing on a trellis, lamppost or gazebo.

The new variety can be readily distinguished from its 'Meiviolin' parental variety. More specifically, the new variety forms larger blossoms having substantially more petals in an ancient rose configuration. Also, the blossoms of the 'Meiviolin' variety are edged with carmine pink coloration unlike the new variety. The new variety additionally can be readily distinguished from the 'Meicharvin' variety (non-patented in the United States). For instance, the 'Meicharvin' variety is considerably less floriferous than the new variety.

The new variety has been found to undergo asexual propagation at Le Cannet des Maures, Var, France, by a number of routes, including budding, grafting, and by the use of cuttings. Asexual propagation by the above-mentioned techniques at such location has shown that the characteristics of the new variety are firmly fixed and are stably transmitted by such asexual propagation from one generation to another. Accordingly, the new variety asexually reproduces in a true to type manner.

The new variety has been named the 'Meiviowit', and is being marketed under the WHITE EDEN trademark.

BRIEF DESCRIPTION OF THE PHOTOGRAPHS

The accompanying photographs show, as nearly true as it is reasonably possible to make the same in color illustrations of this character, typical specimens of the new variety. The rose plants of the new variety were approximately two years of age and were photographed during September while growing outdoors on *Rosa froebelli* rootstock at Le Cannet des Maures, Var, France. Dimensions in centimeters are included at the bottom of each photograph.

FIG. 1 illustrates a specimen of a young shoot,

FIG. 2 illustrates a specimen of a floral bud before the opening of the sepals, FIG. 3 illustrates a specimen of a floral bud at the opening of the sepals, FIG. 4 illustrates a specimen of a floral bud at the opening of the petals, FIG. 5 illustrates a specimen of a flower in the course of opening, FIG. 6 illustrates specimen of an open flower—plan view—obverse, FIG. 7 illustrates a specimen of an open flower—plan view—reverse, FIG. 8 illustrates a specimen of a fully open flower—plan view—obverse, FIG. 9 illustrates a specimen of a fully open flower—plan view—reverse, FIG. 10 illustrates a specimen of a floral receptacle showing the arrangement of the stamens and pistils, FIG. 11 illustrates a specimen of a floral receptacle showing the arrangement of the pistils (stamens removed), FIG. 12 illustrates a specimen of a flowering stem, FIG. 13 illustrates a specimen of a main branch, FIG. 14 illustrates a specimen of a leaf with 3 leaflets—plan view—upper surface, FIG. 15 illustrates a specimen of a leaf with 5 leaflets—plan view—under surface, and FIG. 16 illustrates a specimen of a leaf with 7 leaflets—plan view—upper surface.

DETAILED DESCRIPTION

The chart used in the identification of colors is that of The Royal Horticultural Society (R.H.S. Colour Chart), London, England. The description is based on the observation of two year-old plants during September while growing outdoors on *Rosa froebelli* rootstock at Le Cannet des Maures, Var, France.

Class: Climbing Shrub.

Plant:

*Height.*—Approximately 175 to 190 cm on average at the end of the growing season.

*Width.*—Approximately 60 to 70 cm on average at the end of the growing season.

*Habit.*—Climbing.

Branches:

*Color.*—Young stems: near Yellow-Green Group 146D. Adult wood: near Yellow-Green Group 146C.

*Texture.*—Young stems are smooth and adult wood tends to be rough.

*Thorns.*—Quantity: typically none on young stems and approximately one on average on an adult stem having a length of 10 cm. Length: approximately 0.25 cm on average. Configuration: longish-pointed on the upper surface, and concave on the under surface with an oval base. Color: near Greyed-Orange Group 173C.

Leaves:

*General appearance.*—Dense, medium green, and semi-glossy.

*Size.*—A seven-leaflet leaf commonly is approximately 7 cm in length on average, and approximately 3 cm in width on average.

*Petioles.*—Length: approximately 2 cm on terminal leaflet. Upper surface: near Yellow-Green Group 145B, and non-glandular. Under surface: near Yellow-Green Group 146C, and commonly bear a few prickles.

*Stipules.*—Texture: smooth. Length: commonly approximately 1 cm on average. Width: commonly approximately 0.4 cm on average. Upper surface: near Yellow-Green Group 144D. Under surface: near Yellow-Green Group 146C.

*Leaflets.*—Number: 3, 5, and 7 (most often). Size: terminal leaflets commonly are approximately 4.5 cm in length on average, and approximately 2.5 cm in width on average. Arrangement: alternate and odd pinnately compound. Shape: generally oval (as illustrated). Apex: pointed and cuspidate. Base: obtuse. Margin: serrulate with simple and regular serration. Texture: generally smooth between venation and firm. Color (new foliage): Upper surface: near Green Group 137C suffused with Greyed-Purple Group 183C. Under surface: near Yellow-Green Group 146C suffused with Greyed-Purple Group 183C. Color (adult foliage): Upper surface: near Green Group 137A. Under surface: near Yellow-Green Group 146B.

Inflorescence:

*Number of flowers.*—Typically approximately 1 to 3 per stem.

*Peduncle.*—Smooth, strong, commonly approximately 4.5 cm in length on average, approximately 0.3 cm in diameter on average, and near Yellow-Green Group 146D in coloration.

*Sepals.*—Number: 5. Extensions: few and very small in size. Shape: with a long narrow point and commonly incurved at the base. Size: typically approximately 2 cm in length. Texture: smooth on both surfaces. Color (upper surface): near Yellow-Green Group 146B. Color (under surface): near Yellow-Green Group 146D.

*Buds.*—Shape: globular. Size: medium. Length: approximately 2.5 cm on average. Diameter: approximately 2 cm on average at the widest point. Color: as the calyx breaks near Yellow-White Group 158B and 158C on the upper surface, near Yellow-White Group 158D on the under surface, and the basal spot is near Yellow Group 2C on both surfaces.

*Flower.*—Shape: cup-shaped in an ancient rose configuration. Diameter: approximately 12 to 13 cm on average when fully open. Color (in course of opening): Upper surface: near Yellow-White Group 158D. Under surface: near Yellow-White Group 158D. Basal spot: near Yellow Group 2C. Color (open blossom): Upper surface: near Yellow-White Group 158D. Lower surface: near Yellow-White Group 158D. Basal spot: Upper surface: near Yellow Group 2C. Under surface: near Yellow Group 2D. Color stability: very good with little discoloration upon maturity. Fragrance: very slight. Petal number: commonly at least 100 under normal growing conditions, and typically approximately 103 to 105 on average. Petal arrangement: imbricated. Petaloids: commonly present at the center. Petal texture: relatively firm. Petal margin: entire. Petal apex: reflected. Petal base: obtuse. Petal size: typically approximately 4 cm in length on average, and approximately 3.4 cm in width on average. Petaloid number: approximately seven on average. Petaloid size: commonly approximately 2.5 cm in length and approximately 1.5 cm in width on average. Petaloid color: on the upper surface near Yellow-White Group 158B and 158C, and on the under surface near Yellow-White Group 158D. Anther number: approximately 117 on average and regularly arranged around the styles. Anther size: approximately 0.2 cm on average. Anther color: near Yellow-Orange Group 17A. Filaments: approximately 0.4 cm in length, and near Yellow-Orange Group 17B in coloration. Pollen: present, and near Yellow-Orange Group 17A in coloration. Style number: approximately 68 on average. Style length: approximately 0.3 to 0.5 cm on average. Style color: Red Group 47C. Stigma size: approximately 0.1 cm on average. Stigma color: near Red Group 47D. Lastingness: the blossoms commonly last approximately three weeks on the plant. Petal drop: very good with the petals detaching cleanly before drying. Receptacle: smooth in surface texture, funnel-shaped, approximately 1 cm in length on average, approximately 1.2 cm in width at the widest point on average, and near Yellow-Green Group 146D in coloration. Hips: generally round, approximately 2 cm in length on average, and near Yellow-Green Group 146C in coloration.

Development:

*Vegetation.*—Very strong.

*Blooming.*—Abundant and substantially continuous.

*Aptitude to bear fruit.*—Normal.

*Resistance to diseases.*—Good with respect to Black Spot.

Plants of the 'Meiviowit' variety have not been observed under all possible environmental conditions to date. Accordingly, it is possible that the phenotypic expression may vary somewhat with changes in light intensity and duration, cultural practices, and other environmental conditions without variance in the genotype.

I claim:

1. A new and distinct rose plant characterized by the following combination of characteristics:

(a) exhibits a climbing shrub growth habit, (b) abundantly forms on a substantially continuous basis attractive near white long-lasting very double blossoms having an ancient rose configuration, (c) forms vigorous medium green semi-glossy foliage that contrasts well with the near white blossom coloration, (d) displays good tolerance to frost, and (e) is well suited for providing attractive ornamentation in the landscape;

substantially as herein shown and described.

* * * * *

1 2 3 4 5 6 7 8 9 10 11 12 13 14 15
MEIVIOWIT